United States Patent [19]

Kokubo et al.

[11] Patent Number: 5,068,122
[45] Date of Patent: Nov. 26, 1991

[54] PROCESS FOR FORMING A BIOACTIVE HYDROXYAPATITE FILM

[75] Inventors: Tadashi Kokubo, Nagaokakyo City; Takao Yamamuro, Muko City; Yoshio Abe, Kyoto City, all of Japan

[73] Assignee: Kyoto University, Kyoto City, Japan

[21] Appl. No.: 435,206

[22] Filed: Nov. 8, 1989

[30] Foreign Application Priority Data

Mar. 29, 1989 [JP] Japan .................... 1-74829

[51] Int. Cl.$^5$ .................... B05D 7/24
[52] U.S. Cl. .................... 427/2; 427/430.1; 623/16
[58] Field of Search .................... 427/2, 430.1; 623/16, 623/16 G

[56] References Cited

U.S. PATENT DOCUMENTS

| 4,366,183 | 12/1982 | Ghommidh et al. | 623/16 |
| 4,518,430 | 5/1985 | Brown et al. | 623/16 |
| 4,775,646 | 10/1988 | Hench et al. | 623/16 |
| 4,861,733 | 8/1989 | White | 623/16 |
| 4,871,384 | 10/1989 | Kasuga | 65/30.1 |
| 4,904,257 | 2/1990 | Mori et al. | 623/16 |
| 4,917,702 | 4/1990 | Scheicher et al. | 623/16 |
| 4,950,294 | 8/1990 | Hakamatsuka | 427/2 |

FOREIGN PATENT DOCUMENTS 53-118411 10/1978 Japan .................... 427/2

OTHER PUBLICATIONS

Proceedings of Fall Meeting, The Ceramic Society of Japan, 1988; pp. 401-402 (w/translation).
9th Annual Meeting of Japanese Society for Biomaterials, 1987; p. 6, (w/translation).
Proceedings of Fall Meeting, the Ceramic Society of Japan, 1988; pp. 417-418 (w/translation).
M. Ogino et al., Journal of Non-Crystalline Solids, vols. 38, 39, part 2, May/Jun. 1980; pp. 673-678, "Formation of calcium phosphate films on silicate glasses".

Primary Examiner—Shrive Beck
Assistant Examiner—Terry J. Owens
Attorney, Agent, or Firm—Fleit, Jacobson, Cohn, Price, Holman & Stern

[57] ABSTRACT

Bone-like, bioactive hydroxyapatite films are formed on any substrates of inorganic, metallic or organic material, by soaking a glass mainly comprising CaO and $SiO_2$ and a substrate arranged in a face-to-face relation, a predetermined distance apart, in an aqueous solution substantially saturated or supersaturated with constituent ions of hydroxyapatite.

1 Claim, 1 Drawing Sheet

PROCESS FOR FORMING A BIOACTIVE HYDROXYAPATITE FILM

BACKGROUND OF THE INVENTION

1. Field of the Invention

The present invention relates to a process for coating medical materials to be used in vivo, such as bone repair materials, intravitally embedding medical instruments or accessories, medical implements, various artificial organs or the like, more particularly, to a process for forming a bioactive hydroxyapatite film having bone-like structure and composition over surfaces of any materials to be used in vivo, inorganic materials, metallic materials or organic materials.

2. Description of the Prior Art

As a process for coating a substrate with hydroxyapatite, there have been generally known plasma spray coating processes (Japanese Patent Application Laid-open Nos. 62-34,559, 62-57,548, and 63-160,663) and processes wherein a substrate is coated with a solution or compound containing Ca and P, followed by sintering (Japanese Patent Application Laid open Nos. 62-231,669, 63-24,952 and 63-46,165). Other than the above, there have been disclosed a sputtering process (Japanese Patent Application Laid-open No. 58-109,049) and, recently, a flame spraying process (Proceedings of Fall Meeting, The Ceramic Society of Japan, 1988, p.p. 401~402), a glass frit firing process (Abstract of 9th Annual Meeting of Japanese Society for Biomaterials, 1987, p.6) and an electrophoretic coating process (Proceedings of Fall Meeting, The Ceramic Society of Japan, 1988, p.p. 417~418).

Each of the above-described prior art processes has disadvantages such as the following or the like:

① in the plasma spray coating process and the flame spraying method, intricate and expensive pieces of equipment are required, dense films are difficult to produce, and the raw material, i.e., hydroxyapatite, is once molten at a high temperature so that the resulting apatite films are different in type from the bone apatite;

② in the sputtering process, also intricate and expensive pieces of equipment are required, and the raw material, hydroxyapatite, is once decomposed due to high energy so that the resulting films are different in type from the bone apatite;

③ in the sintering process or the glass frit firing process, since a heat treatment at around 850° C. is required, only substrates high in heat resistance are applicable and, further, also in this case, the raw material, i.e., hydroxyapatite, is once subjected to a heat treatment at a high temperature so that the resulting apatite films are different in type from the bone apatite; and ④ in the electrophoretic coating process, since substrates themselves are used as an electrode, only good electro-conductive, metallic substrates are applicable, and a sintered apatite is used as a raw material so that the resulting apatite films are also different from the bone apatite.

In the meanwhile, we, the inventors, have already developed a glass-ceramic, by a process for separating out apatite and wollastonite within a glass, which exhibits a bioactivity to spontaneously bond chemically and strongly with bones in vivo within a short period of time and retains a high mechanical strength for a long period of time. In the further pursuit of factors controlling this bioactivity, the inventors have elucidated that what plays an important role when ceramics are bonded with bones is not a apatite phase existing in the glass-ceramics that is formed by glass crystallizing process but a bone-like apatite layer newly depositing on the surface of the glass-ceramics by reacting with ambient body fluid when they are embedded in the living body. Further, it has been found that this apatite layer can be produced only by soaking the glass-ceramics to be bonded with the bones in an aqueous solution not containing cells but having only its inorganic ion concentration made to be equivalent to the human body fluid, and that Ca and Si eluting from the glass-ceramic play a very important role for producing this apatite layer. Based on these findings, the inventors have conducted assiduous studies to form a bone-like apatite layer on the surface of various substrates and eventually accomplished the present invention.

SUMMARY OF THE INVENTION

The object of the present invention is to provide a very simple process for readily depositing bone-like, bioactive apatite films on substrates of any material, inorganic, metallic or organic, without heat treatment being conducted.

The above object can be achieved by the process comprising: arranging a substrate and a glass comprising CaO and SiO$_2$ as main components, in a face-to-face relation, a predetermined distance apart; and soaking the thus arranged substrate and glass in an aqueous solution substantially saturated or supersaturated with constituents of hydroxyapatite to deposit a bone-like hydroxyapatite film on the surface of the substrate.

In the process of the invention, the glass preferably comprises 20~60 mol % CaO and 40~80 mol % SiO$_2$ and the total amount of CaO and SiO$_2$ is at least 70 mol %.

The above aqueous solution preferably contains Ca and P, as a solute, in amounts of 0.1~10 mM as Ca$^{2+}$ ion and 0.1~50 mM as HPO$_4^{2-}$ ion, respectively.

The aqueous solution is preferably at a pH ranging from 5 to 9.

Further, the aqueous solution is preferably at a temperature ranging 5 to 70° C.

The distance between the substrate and the glass preferably does not exceed 2 mm.

BRIEF DESCRIPTION OF THE DRAWING

The invention will now be described with reference to the accompanying drawing wherein.

DETAILED DESCRIPTION OF THE INVENTION

Figure 1:
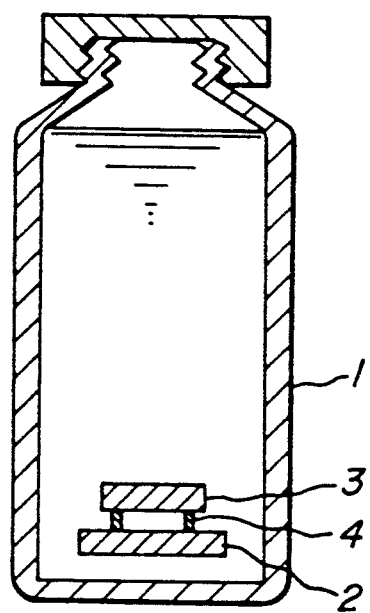
FIG. 1 is a vertical cross-sectional view illustrating an embodiment of an apparatus for conducting the process of the present invention.

In order to conduct efficiently the process of the present invention, it is preferred to limit the composition of the glass to face the substrate, the ion concentration, pH and temperature of the aqueous solution for the substrate to be soaked in and further the distance between the substrate and the glass, respectively, in predetermined ranges.

On the outset, the glass suitable for the object of the present invention is required to comprise CaO and SiO$_2$ as a main component. Typical compositions of the glass are shown in Table 1. In Table 1, Samples 1~3 are glasses containing only CaO and SiO$_2$. Sample 4 contains P$_2$O$_5$ other than CaO and SiO$_2$. Sample 5 has the composition same as the Bioglass ®. Sample 6 has the composition same as the bioactive glass-ceramic the inventors have formerly developed. Samples 7~15 are glasses comprising CaO and SiO$_2$ as a main component and Na$_2$O, K$_2$O, MgO, P$_2$O$_5$, etc. in various amounts. Any of the above glasses have an ability to form a hydroxyapatite film on various substrates. However, when CaO is less than 20 mol %, the film formability of the glass becomes too low, and when it is in excess of 60 mol %, the glass is difficult to produce. Alternatively, when SiO$_2$ is less than 40 mol %, the glass is also difficult to produce, and when it is in excess of 80 mol %, the film formability is too low, and either when Ca$^{2+}$ exceeds 10 mM or HPO$_4^{2+}$ exceeds 50 mM, the hydroxyapatite precipitates everywhere in the aqueous solution and the films tend to be not formed on the objective substrates. Therefore, Ca$^{2+}$ and HPO$_4^{2-}$ are preferably limited to 0.1~10 mM and 0.1~50 mM, respectively. Important ions as a solute of the aqueous solution are Ca$^{2+}$ and HPO$_4^{2-}$. Other than the above, ions such as Na$^+$, K$^+$, Mg$^{2+}$, Cl$^-$, HCO$_3^-$, SO$_4^{2-}$ or the like may be contained. However, it is most preferred for the aqueous solution to have the pseudohumoral blood plasma composition shown in Composition 13, in order to keep the condition of stabilized ionic solution for a long period of time.

TABLE 2

| Ion | Ion concentration of aqueous solution (mM) | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Ca$^{2+}$ | 0.1 | 10 | 0.1 | 10 | 0.1 | 10 | 0.5 | 5 | 10 | 0.5 | 5 | 10 | 2.5 |
| HPO$_4^{2-}$ | 0.1 | 0.1 | 5 | 5 | 50 | 50 | 1 | 1 | 1 | 10 | 10 | 10 | 1 |
| Na$^+$ | 0 | 0 | 0 | 0 | 0 | 0 | 51 | 104 | 5.2 | 159 | 100 | 4.2 | 142 |
| K$^+$ | 0 | 0 | 0 | 0 | 0 | 0 | 5 | 0 | 1 | 0 | 3 | 0 | 5 |
| Mg$^{2+}$ | 0 | 0 | 0 | 0 | 0 | 0 | 0 | 2 | 0 | 1 | 0 | 1.5 | 1.5 |
| Cl$^-$ | 0 | 0 | 0 | 0 | 0 | 0 | 55 | 113 | 20 | 152 | 113 | 13 | 155.3 |
| HCO$_3^-$ | 0 | 0 | 0 | 0 | 0 | 0 | 0 | 4.2 | 4.2 | 0 | 0 | 4.2 | 4.2 |
| SO$_4^{2-}$ | 0 | 0 | 0 | 0 | 0 | 0 | 0.5 | 0 | 0.5 | 0 | 0.2 | 0 | 0.5 | the hydroxyapatite film formability of the glass becomes too low. Further, when the total amount of CaO and SiO$_2$ is less than 70 mol %, the hydroxyapatite formability of the glass decreases extremely. Therefore, it is preferred that CaO is in 20~60 mol %, SiO$_2$ is in 40~80 mol % and the total amount of CaO and SiO$_2$ is at least 70 mol %.

Further, as regards the pH of the aqueous solution, the hydroxyapatite is known to be unstable in the acidic zone and to precipitate stably in the neutral or alkaline zone. In the case where hydroxyapatite films are formed according to the process of the present invention, the aqueous solution upon preparation generally differs in pH from that after soaking of the glass and

TABLE 1

| Component | Composition of glass (mol %) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| CaO | 20 | 50 | 60 | 57.21 | 26.91 | 49.87 | 20 | 40 | 55 | 20 | 30 | 40 | 20 | 25 | 30 |
| SiO$_2$ | 80 | 50 | 40 | 35.60 | 46.14 | 35.46 | 70 | 50 | 40 | 60 | 50 | 40 | 50 | 45 | 40 |
| P$_2$O$_5$ | 0 | 0 | 0 | 7.182 | 2.600 | 7.153 | 30 | 0 | 5 | 10 | 10 | 10 | 10 | 10 | 10 |
| Na$_2$O | 0 | 0 | 0 | 0 | 24.35 | 0 | 0 | 5 | 5 | 0 | 5 | 0 | 5 | 10 | 0 | 10 |
| MgO | 0 | 0 | 0 | 0 | 0 | 7.111 | 15 | 0 | 0 | 5 | 5 | 0 | 10 | 10 | 0 |
| K$_2$O | 0 | 0 | 0 | 0 | 0 | 0 | 0 | 5 | 0 | 0 | 5 | 5 | 0 | 10 | 10 |
| CaF$_2$ | 0 | 0 | 0 | 0 | 0 | 0.399 | 0 | 0 | 0 | 0 | 0 | 0 | 0 | 0 | 0 |

Further, the aqueous solution suitable for the object of the present invention is required to contain at least main constituents of apatite in a substantially saturated or supersaturated concentration. Herein, the term, "substantially saturated or supersaturated concentration" is to be understood to mean a concentration that is close to and functions substantially equivalently to the saturated concentration. Particularly important, inter alia, of the above main constituents of the apatite are Ca$^{2+}$ and HPO$_4^{2-}$ ions. Examples of the constituents are shown in Table 2. In Table 2, Compositions 1 to 6 are aqueous solutions containing only Ca$^{2+}$ and HPO$_4^{2-}$. Compositions 7 to 12 are aqueous solutions containing Na$^+$, K$^+$, Mg$^{2+}$ Cl$^-$, HCO$_3^-$, SO$_4^{2-}$, etc. in various amounts, other than Ca$^{2+}$ and HPO$_4^{2-}$. Composition 13 has an ion concentration substantially equivalent to the human blood plasma. Any of these has an ability of forming hydroxyapatite films on various substrates. However, when Ca$^{2+}$ or HPO$_4^{2-}$ is less than 0.1 mM, changes towards pH increase due to elution of constituents of the glass during the soaking, as shown in Table 3. The pH is preferred to be at least 7 after the soaking in order to form hydroxyapatite films. For achieving this, the aqueous solution is recommended to have a pH of at least 5 upon preparation. Further, if the pH exceeds 9 upon preparation, then hydroxyapatite almost spontaneously precipitates everywhere in the aqueous solution so that the films are hardly formed. Accordingly, the suitable pH value of the aqueous solution is in the range of 5~9. It is desired that the pH of the solution substantially does not change from the time of the preparation through the completion of the hydroxyapatite film formation. For this purpose, if a buffering agent, for example, comprising 50 mM of tris(hydroxymethyl)aminomethane [(CH$_2$OH)$_3$CNH$_2$] and 45 mM of hydrochloric acid (HCl) is added to the aqueous solution, the pH is effectively maintained in the range of 7~9.

TABLE 3

| Relation between pH and film formation | | | | | | | | |
|---|---|---|---|---|---|---|---|---|
| pH upon preparation | 4.0 | 5.1 | 6.3 | 7.0 | 7.5 | 8.1 | 8.9 | 9.3 |
| pH after soaking | 6.1 | 7.0 | 7.2 | 7.6 | 7.9 | 8.8 | 9.5 | 9.8 |

TABLE 3-continued

| Relation between pH and film formation | | | | | | | |
| --- | --- | --- | --- | --- | --- | --- | --- |
| Apatite film covering ratio on substrate (%) | 0 | 90 | 99 | 100 | 100 | 100 | 100 | 0 |

Further, as regards the temperature of the aqueous solution, it is known that the solubility of the hydroxyapatite decreases as the temperature increases. The gist of the process according to the invention lies in that a glass is soaked in an aqueous solution substantially saturated or supersaturated with hydroxyapatite and the degree of supersaturation is gradually heightened by virtue of elution of glass constituents. As the temperature of the aqueous solution is lowered, the solubility will increase, namely the degree of supersaturation will decrease, and in addition the elution rate of the glass constituents decreases. As shown in Table 4, at lower than 5° C., the covering ratio of the film drastically decreases. Alternatively, the temperature increase readily causes the increase of the degree of supersaturation, whereas if the temperature exceeds 70° C, the phase of the film turns to a non-single phase of hydroxyapatite. Accordingly, the suitable temperature of the aqueous solution lies in the range of 5~70° C.

TABLE 4

| Relation between temperature of aqueous solution and film formation | | | | | | | |
| --- | --- | --- | --- | --- | --- | --- | --- |
| Temperature (°C.) | 3 | 5 | 10 | 30 | 50 | 70 | 75 |
| Apatite film covering ratio on substrate (%) | 5 | 70 | 80 | 100 | 100 | 80 | 70 |
| Phase of film | HAp | HAp | HAp | HAp | HAp | HAp | HAp, CC |

(Note)
HAp: Hydroxyapatite
CC: Calcium carbonate hexahidrate

Furthermore, as regards the distance between the substrate and the glass, whereas the gist of the process according to the present invention, as mentioned above, lies in the increase of the supersaturation degree of the hydroxyapatite constituents by virtue of the elution of the glass constituents, the more remote the glass is, the lower will be the degree of supersaturation in the vicinity of the substrate. As shown in Table 5, when the distance between the substrate and the glass exceeds 2 mm, the covering ratio of apatite film on substrate extremely decreases. Accordingly, the distance between the substrate and the glass is preferred to be not exceeding 2 mm.

TABLE 5

| Relation of covering ratio with distance between substrate and glass | | | | | | | |
| --- | --- | --- | --- | --- | --- | --- | --- |
| Distance (mm) | 0.01 | 0.1 | 0.5 | 1.0 | 1.5 | 2.0 | 2.2 | 2.5 |
| Apatite film covering ratio on substrate (%) | 100 | 100 | 100 | 100 | 95 | 90 | 20 | 0 |

The material and shape of the substrate to be applied to the process according the present invention are not particularly limited. Namely, the material of the substrate may be any of inorganic, metallic and organic. Further, the shape of the substrate may be not only a flat plate but also convex, concave or intricate shapes of combination thereof.

The present invention will be explained hereinafter in more detail by way of example.

EXAMPLE 1

Calcium carbonate, calcium fluoride, silica and calcium phosphate, weighed out in accordance with the composition of Sample 6 of Table 1, were mixed together and then put into a platinum crucible wherein the mixture was molten at 1450° C for 2 hours. The molten liquid was cast on an iron plate and covered with another iron plate to produce a sheet of plateglass. A sample plate of 10 mm × 15 mm × 2 mm cut out from the plateglass and a substrate of alumina sintered body having approximately the same size were arranged and fixed in a face-to-face relation, 0.5 mm apart, using spacers of alumina ceramic. Then, sodium chloride, sodium carbonate, potassium chloride, potassium phosphate, magnesium chloride and calcium chloride were weighed out in accordance with Composition 13 of Table 2 and dissolved into ion-exchanged water to prepare an aqueous solution. The aqueous solution was admixed with 50 mM of tris(hydroxymethyl)aminomethane and 45 mM of hydrochloric acid as a buffering agent to maintain the pH of the solution at 7.25. As shown in FIG. 1, 100 ml of the obtained aqueous solution was measured out and put into a container 1 made of polyethylene. Then, previously prepared glass 2 and a substrate 3 arranged in a face-to-face relation, kept 0.5 mm apart by means of spacers 4, were soaked in the aqueous solution and held in a thermostatic chamber at 36.5° C. After 3 days, the substrate was taken out of the aqueous solution, washed briefly with ion-exchanged water and dried at room temperature for half a day. A bioactive hydroxyapatite film was obtained, through the above simple procedure, on the surface opposite to the glass, of the substrate. The properties of the film are shown in Table 6.

TABLE 6

| Properties of hydroxyapatite film | | |
| --- | --- | --- |
| Thickness of film | Covering ratio on substrate | Bond strength (tensile) |
| 1~2 μm | 99~100% | 8~10 MPa |

EXAMPLE 2

A plateglass and an aqueous solution were obtained in the same manner as Example 1. Then, using various substrates shown in Table 7, whether films were formed or not was examined. The result is shown in Table 7 together with the evaluation result.

TABLE 7

Properties of film depending on substrate

| Substrate | Thickness of film (μm) | Covering ratio on substrate (%) | Bond strength (tensile) (MPa) |
|---|---|---|---|
| Silica glass | 1~1.5 | 99~100 | 9~11 |
| Slide glass | 1~1.5 | 99~100 | 9~11 |
| Sintered-Alumina | 1~1.5 | 99~100 | 8~10 |
| Sintered-Zirconia | 1~1.5 | 99~100 | 8~10 |
| Pt metal | 1.5~2 | 99~100 | 3~4 |
| Au metal | 1.5~2 | 99~100 | 3~4 |
| 316 St. st. | 1.5~2 | 99~100 | 3~4 |
| Ti metal | 1.5~2 | 99~100 | 3~4 |
| Ti—6Al—4V alloy | 1.5~2 | 99~100 | 3~4 |
| Polymethylmethacrylate | 0.5~1 | 99~100 | 0.5~1 |
| Polyethylene | 0.5~1 | 99~100 | 0.5~1 |

EXAMPLE 3

A plateglass and an aqueous solution were obtained in the same manner as Example 1. An alumina substrate and the plateglass were arranged in a face-to-face relation as Example 1 and conditions of film formation were examined, varying the quantity of the aqueous solution. The experimental conditions and the result are shown together in Table 8. As seen in Table 8, the film is formed even if the quantity of the solution largely increases.

TABLE 8

Conditions of film formation depending on quantity of solution

| Quantity of solution (ml) | Thickness of film (μm) | Covering ratio on substrate (%) |
|---|---|---|
| 10 | 1.0 | 99~100 |
| 20 | 1.5 | 99~100 |
| 40 | 1.5 | 99~100 |
| 100 | 1.5 | 99~100 |
| 200 | 1.5 | 99~100 |

As explained and demonstrated above, according to the process of the present invention, any substrates of inorganic, metallic or organic, irrespective of its material, can be very readily coated with a bone-like, bioactive apatite film without heat treatment being conducted. Further, the bone-like apatite films coated on the substrates re excellent not only in bondability with bone tissue but also in compatibility with soft tissue such as epidermis, muscle or the like. Therefore, bone repair materials, intravitally embedding medical instruments or accessories, medical implements, various artificial organs or the like, which are coated with the bioactive, hydroxyapatite films according to the process of the present invention, exhibit excellent effects as a medical material.

What is claimed is:

1. A process for forming a bioactive hydroxyapatite film on a surface of a substrate, comprising the steps of:
    arranging the substrate and a glass comprising 20-60 mol % CaO and 40-80 mol % SiO$_2$, wherein the total amount of CaO and SiO$_2$ in the glass is at least 70 mol %, in a face-to-face relation at a distance of at most 2 mm apart; and
    soaking the thus arranged substrate and glass in an aqueous solution comprising hydroxyapatite constituents Ca and P as a solute in amounts of 0.1-10 mM as Ca$^{+2}$ ion and 0.1-50 mM as HPO$^{-2}$ ion, at a pH in the range of 5-9 and a temperature in the range from 5-70° C. to form a bone-like hydroxyapatite film on the surface of the substrate, wherein the positioning of the substrate surface near the glass surface provides a concentration of hydroxyapatite constituents at the substrate surface which is higher than the concentration in the bulk of the solution.

* * * * *